US009555812B2

(12) United States Patent
Parchami

(10) Patent No.: US 9,555,812 B2
(45) Date of Patent: Jan. 31, 2017

(54) METHOD FOR DETECTING A ROADWAY AND CORRESPONDING DETECTION SYSTEMS

(71) Applicant: Robert Bosch GmbH, Stuttgart (DE)

(72) Inventor: Marzieh Asadeh Parchami, Leonberg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 14/744,678

(22) Filed: Jun. 19, 2015

(65) Prior Publication Data
US 2015/0367855 A1    Dec. 24, 2015

(30) Foreign Application Priority Data
Jun. 24, 2014 (DE) ........................ 10 2014 212 032

(51) Int. Cl.
*G01N 21/55* (2014.01)
*B60W 40/068* (2012.01)
*G01S 17/46* (2006.01)
*G01S 17/93* (2006.01)
*G06T 7/00* (2006.01)
*G06F 19/00* (2011.01)
*G01N 21/17* (2006.01)

(52) U.S. Cl.
CPC ............ *B60W 40/068* (2013.01); *G01N 21/55* (2013.01); *G01S 17/46* (2013.01); *G01S 17/936* (2013.01); *G06T 7/0004* (2013.01); *B60W 2420/403* (2013.01); *B60W 2520/26* (2013.01); *B60W 2550/141* (2013.01); *B60W 2550/148* (2013.01); *B60W 2720/26* (2013.01); *G01N 2021/1765* (2013.01); *G01N 2021/551* (2013.01); *G06T 2207/30256* (2013.01)

(58) Field of Classification Search
CPC .......... G01N 21/55; G01N 21/95; G06F 19/00
USPC ....................................... 701/36, 1; 348/149
See application file for complete search history.

(56) References Cited

U.S. PATENT DOCUMENTS

| | | | | |
|---|---|---|---|---|
| 5,218,206 A | * | 6/1993 | Schmitt | B60R 16/0237 250/339.1 |
| 5,489,777 A | * | 2/1996 | Stedman | G01J 5/602 250/330 |
| 6,281,632 B1 | * | 8/2001 | Stam | B60Q 1/085 250/208.1 |
| 2008/0129541 A1 | * | 6/2008 | Lu | G06K 9/00791 340/905 |

(Continued)

*Primary Examiner* — Tan Q Nguyen
(74) *Attorney, Agent, or Firm* — Norton Rose Fulbright US LLP; Gerard Messina

(57) ABSTRACT

A method is provided for detecting a roadway of a vehicle including at least the following steps: generating a light signal and emitting the light signal onto a lit area of the roadway, receiving retroreflected radiation of the lit area and generating an image signal, evaluating the image signal. For this purpose, it is provided that the light signal having light structures is generated, the image signal is evaluated as a two-dimensional light pattern, a detection of pattern characteristics corresponding to the light structures being carried out in the light pattern during the evaluation of the image signals, a signal strength of the image pattern being evaluated in a space-resolved manner and a reflecting behavior of the lit area being inferred therefrom, and a roadway surface being inferred from the reflecting behavior.

20 Claims, 3 Drawing Sheets

(56) References Cited

U.S. PATENT DOCUMENTS

2009/0116259 A1* 5/2009 Ohshio ............... F21S 48/1794
362/512

* cited by examiner

METHOD FOR DETECTING A ROADWAY AND CORRESPONDING DETECTION SYSTEMS

FIELD OF THE INVENTION

The present invention relates to a method for detecting a roadway and a corresponding detection system.

BACKGROUND INFORMATION

The detection of the roadway enables in particular an assessment of the roadway surface in order to, for example, be able to estimate the friction coefficient or disadvantageous properties of the roadway.

In this area, detection systems are known which assess the behavior of preceding vehicles and/or ascertain information from traffic messages and output warnings regarding possible slippery wintry conditions to the driver. Here, the ITS—Intelligent Transport System—is known, among others.

Furthermore, it is known to apply a roadway surfacing on the roadway, which changes color in the case of slippery wintry conditions and thus represents a directly perceivable warning. However, it is disadvantageous that a specific surfacing has to be applied on the roadway and must be maintained. It is also possible for the color or wavelength and intensity distribution of the light emitted by the roadway to be a function of additional factors.

Furthermore, detection systems are known in which an ultrasound noise, which arises from friction of the tires against the roadway, is recorded and assessed.

Furthermore, camera systems are known which detect the roadway. It is known here that the roadway is lit by, for example, a headlight, and at least one part of the lit area of the roadway is detected by the camera. Furthermore, additional road users may be detected and their driving behavior assessed. The detection of, for example, slippery wintry conditions, is generally, however, not possible.

Known systems thus enable in particular no flexible and rapid reaction of the driver to an instantaneously present roadway surfacing such as water or ice. Furthermore, known systems, such as the marking of the road surface and similar measures at the roadway surface are complex and may not be carried out for all roads of a traffic system.

SUMMARY

According to the present invention, a light signal having light structures is generated and transmitted onto the roadway and an image signal is recorded which contains light reflected from the roadway, the image signal being recorded as a two-dimensional light pattern and evaluated. During the evaluation, pattern characteristics corresponding to the light structures may be ascertained in the light pattern and assessed.

Pattern characteristics corresponding to the light structures are here pattern characteristics, i.e., structures of the light pattern, which result from the projection onto the roadway at an angle of incidence and subsequent recording with a camera, which is preferably slightly offset from a pattern generator generating the light signal.

Several Advantages are Achieved According to the Present Invention:

A light pattern may be recorded and evaluated which enables an unambiguous, spatially resolved assignment of the points of the pattern to points or places in the lit area of the roadway and thus a relative position with respect to the vehicle.

The lit area of the roadway may thus be rated based on different assessment criteria.

For one, the temporal behavior of the image signal and the signal strength of the reflected light may be assessed so that a change of the roadway surface may be inferred.

Furthermore, the signal strength of the reflected light may be evaluated in a space-resolved manner. For this purpose, measured values from a calibration are advantageously available so that a direct evaluation of the signal strength is possible due to the calibration. A distance of the detected point, i.e., in particular, a distance to the vehicle may be inferred from the signal strength. Furthermore, a reflected behavior of the roadway surface and thus a reflectance may be inferred from the signal strength. From the reflecting behavior, a classification of the roadway surface into different classes having different reflecting behaviors may be carried out. The image of the pattern is in particular determined unambiguously from the signal strength and geometry.

A classification may in particular take place regarding different roadway surfaces having different friction coefficients. For this purpose, relevant classes may in particular be the following: no roadway surfacing/no asphalt, a wet roadway surface/wet conditions, or a film of moisture, and furthermore frozen water. In the case of a classification as frozen water, it may be differentiated between, on the one hand, ice or frost, and, on the other hand, snow, or multiple sub-classes may also be provided, for example, black ice or freezing moisture, cloudy frost or snow.

The present invention is hereby based on the idea that these different roadway surfaces are essentially based on different forms of water; they show different reflecting behavior due to their different states of aggregation, and furthermore have a different reflecting behavior as a function of the crystallization, porosity, turbidity due to air entrapments or entrapments of particles, and furthermore accommodated particles, which enables a classification.

The reflectivity of the individual forms of state of water are sufficiently known, in particular due to data collections which are generally accessible. New snow (without dirt) has the highest reflectance in the NIRS (near-infrared spectrum) in the range of 90% of incident signal strength. In the case of firn or dirty forms of snow, the highest reflectance in the NIRS is at up to 60%. Ice without entrapments (sheet ice or black ice) has a reflectance of approximately 50% in the NIRS. Foggy ice (including entrapments) only has a reflectance in the NIRS in the range of 30%. Water in fluid form has a reflectance in the range of 15% to 20%. With the gradation of the reflectance of the signal strength for the different forms of surfaces, the different surfaces based on water may be divided into classes and differentiated from one another.

Friction coefficients or friction coefficient ranges may subsequently be assigned to the different classes.

By having a signal axis of the pattern generator deviating from the optical axis of the camera, the measurement of the reflectance may be improved since direct reflections at reflective surfaces may be maintained at a lower degree which appear stronger at the same axes and generally do not represent direct material properties.

Furthermore, a geometrical calibration is also possible so that an unambiguous assignment of the point to the lit area of the roadway is possible from the light pattern or from the pattern characteristics of the light pattern. A high spatial resolution may thus be achieved and a classification of the roadway surface may thus be carried out in different areas or distances in front of the vehicle.

In particular a lit area may thus also be covered across a larger distance, for example, from one meter or a few meters in front of the vehicle, i.e., in the image of the camera directly above the hood, up to one hundred meters in front of the vehicle or more, and subsequently a space-resolved classification of the roadway surface may be carried out.

The emitted light is advantageously in a wavelength range above the visible light, in particular in the near infrared spectrum, e.g., in the range of 780 nm to 820 nm.

According to the present invention it is recognized that no interference with the driver of approaching vehicles or other road users occurs in this wavelength range, but that similar image sensors based on CMOS or CCD, for example, have a high light sensitivity.

Furthermore, a camera may be used in this way for a vehicle which also enables wider image recording processing in addition to the detection system.

The pattern generator may in particular be designed including an LED or laser diode for emitting light or radiation in the relevant wavelength range, and include a projection lens which has a diffractive optical element whose manufacture is enabled by lithographic methods. In this way in particular a light signal may be formed having light structures which then represent a light pattern having specific pattern characteristics in the image of the camera, which allows an unambiguous resolution and image processing, in particular a space-resolved image processing.

In particular lines may be generated as pattern characteristics which show themselves as straight lines in the image, since deviations from a straight line may be easily recognized and detected by image processing logarithms.

In particular multiple lines are generated which essentially run alongside the roadway, or, in the picture, in a vertical direction, i.e., away from the vehicle, for example, some lines being able to be parallel and other lines at an angle to them. Advantageously, at least some of the lines intersect at characteristic intersection points or intersecting angles so that an evaluation of the angles is possible in the intersecting angles during the image processing and evaluation.

From the pattern characteristics it may initially be ascertained whether a proper image is present which appears at a level roadway as a projection, or whether an obstacle is present, for example, also an additional road user who causes a change of the geometry of the pattern characteristics.

Furthermore, the space-resolved assignment to areas of the roadway, in particular, distances to the host vehicle, may be carried out.

It is also possible to detect larger irregularities and, for example, dirt on the roadway as a deterioration of the pattern characteristics.

The wavelength range may also be vehicle-specific or type-specific, in order to avoid an interference also in this way with corresponding detection systems of other vehicles.

The detection system and the method according to the present invention thus enable in particular a space-resolved detection, in particular including direct assignment to the ground area of the roadway, the local detection including an evaluation of pattern characteristics furthermore allowing an assessment of whether an obstacle is present since an obstacle results in a change in the shape of the pattern characteristics, a resolved detection with respect to the signal strength from which the reflectance may be ascertained and obstacles may be detected, a time-resolved detection from which changes of the roadway surface may be inferred.

A vehicle control system may thus be provided which, due to a classification of the roadway, carries out a vehicle dynamics control or stability control corresponding to an ascertained or estimated friction coefficient, in particular also in different areas in front of the vehicle.

DETAILED DESCRIPTION

Figure 1:
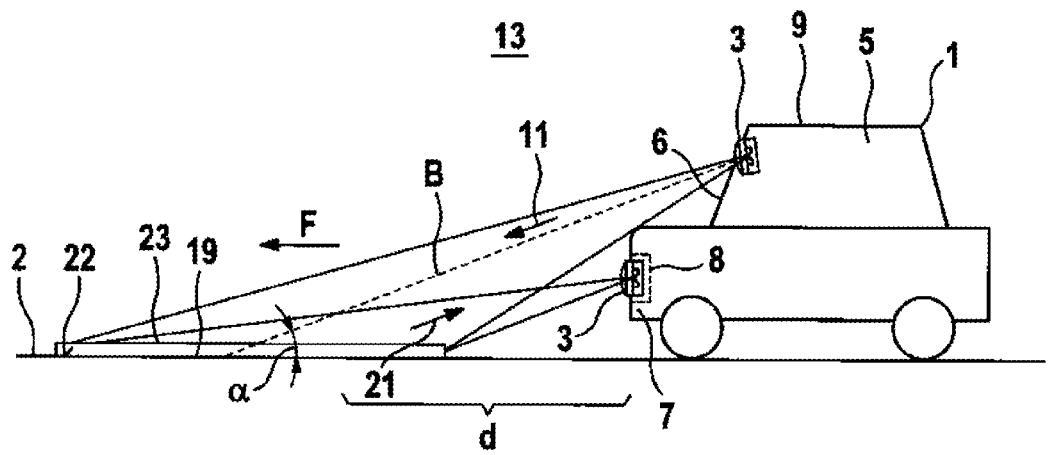
FIG. 1 shows a vehicle including a detection system according to specific embodiments of the present invention while traveling on a roadway.

A vehicle 1 travels on a roadway 2 in a traveling direction F. The vehicle includes a detection system 3, which is provided at the vehicle according to FIG. 1 at different places; for this purpose, the mounting at two preferred positions is shown in FIG. 1:

on the one hand in the interior space 5 (passenger compartment) of vehicle 1 behind a vehicle window 6, in particular of windshield 6, in its wiped area, and, on the other hand, i.e., as an alternative, in front area 7 of the vehicle, e.g., in the area of the bumper; detection system 3 may in particular be integrated into or combined with a headlight 8 (front headlight, head lamp) in front area 7.

Figure 2:
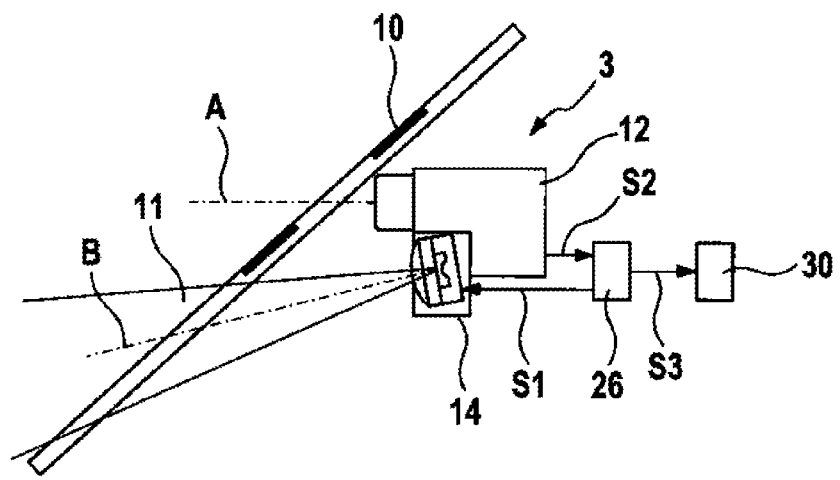
FIG. 2 shows a detection system in detail.

FIG. 2 shows the first mounting in more detail, i.e., at the vehicle window, in particular at a windshield 6. Detection system 3 may in particular be attached close to vehicle roof 9 or at the rearview mirror and/or in a black print area 10 of windshield 6, advantageously in the wiped part of windshield 6 which is not visible for the user.

Detection system 3 includes a camera 12 and a pattern generator 14 which are advantageously mechanically joined or integrated with one another as one unit. Camera 12 may be provided for additional functions, i.e., generally as a multi-purpose camera; it may thus detect the exterior area 13 outside of vehicle 1, also for the visual representation onto a display device of vehicle 1, furthermore for the detection of distances to additional objects, in particular as a stereo camera, as well as for recording in the infrared spectrum, for example, using night vision function.

Figure 4:
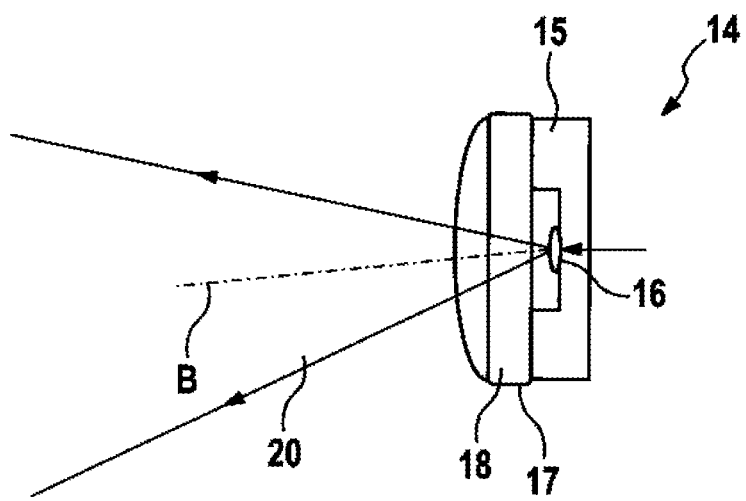
FIG. 4 shows a pattern generator according to a specific embodiment.

FIG. 4 shows the design of pattern generator 14: Pattern generator 14 includes a housing 15, an LED 16 or a laser diode and a projection lens 17 which advantageously includes a diffractive optical element (DOE) 18. Projection lens 17 may generally, in addition to diffractive optical element 18, also include other optical elements for generating a suitable projection geometry. LED 16 or the laser diode thus emits light in a narrow-band spectral range as light source of pattern generator 14, in particular of one single, central wavelength $\lambda m$ which is advantageously in the non-visible range, in particular in the near infrared spectrum, for example, in the wavelength range between 780 nm and 820 nm. Pattern generator 14 thus generates a light signal 11 including light structures 19, light signal 11 being invisible to the human eye but easily generated with equipment since sensors based on silicon are sufficiently sensitive in this spectral range.

Furthermore, it is evident that such a wavelength range compliments wavelength ranges well which are usable by a camera for additional functions, in particular a night vision function, but also an image detection in the visible wavelength range.

The wavelength range of the near infrared spectrum of 780 nm to 820 nm is furthermore also advantageous, since different roadway surfaces 22 to be detected on roadway 2 here have relevant characteristics or properties. In this wavelength range, in particular reflectance r_ice of frost or ice as roadway surface 22 is in the range of approximately 60% to 90%. Reflectance r_ice is thus higher by approximately 50% to 80% than reflectance r0 of asphalt as common material of roadway 2 which is in the range of approximately 10%.

Furthermore it is evident that different types of ice or frost also show a different reflectance r. Cloudy frost thus shows a different reflectance r_ice_1 than reflectance r_ice_2 of freezing moisture; furthermore, reflectance r_ice_3 of black ice, which occurs due to rapid or immediate freezing of liquid precipitation or rain onto a roadway 2 at low temperatures significantly below 0° C., shows a deviating value. These types of iciness or different forms of frost or ice differ in different molecular arrangements of the liquid, in the formed pores or porosity and also as a function of additional particles or a cloudiness.

A roadway surface 22 may thus be differentiated and classified in whether fluid water, i.e., wetness from rain, or frost or ice are present.

The system may here be calibrated for the reflectance of different surfaces or classes of surfaces. The signal strength reflected back may be characterized unambiguously with and without the different surfaces. It is thus possible to ascertain the reflectance of the individual surfaces in the given wavelength range experimentally in advance for the chain of signal processing. The detection system receives a radiometric calibration, i.e., it is known in the detection system which gray scale value of an image sensor corresponds to which input signal strength from the object space of the pattern. The received signal strength of the pattern is preferably compared to the stored and instantaneously measured values. In this way it is possible to make a statement about the condition of the surface due to the signal strength of the pattern.

Pattern generator 14 of detection system 3 advantageously emits light signal 11 having a signal axis B which deviates from optical axis A of camera 12; generally, light signal 11 is emitted forward, i.e., in traveling direction and at an angle to the horizontal which corresponds to angle of incidence α to roadway 2 representing the horizontal. Light signal 11 detects on roadway 2 a lit roadway area 23 of roadway 2 on which it creates a light pattern 19 which thus represents the intersection of light signal 11 expanding in a cone shape and roadway 2. Light pattern 19 in turn emits reflected light 21 which is in turn detected by camera 12. The camera emits image signals S2 to a control device 26 which show themselves according to FIG. 3 as two-dimensional light pattern 20.

Figure 3:
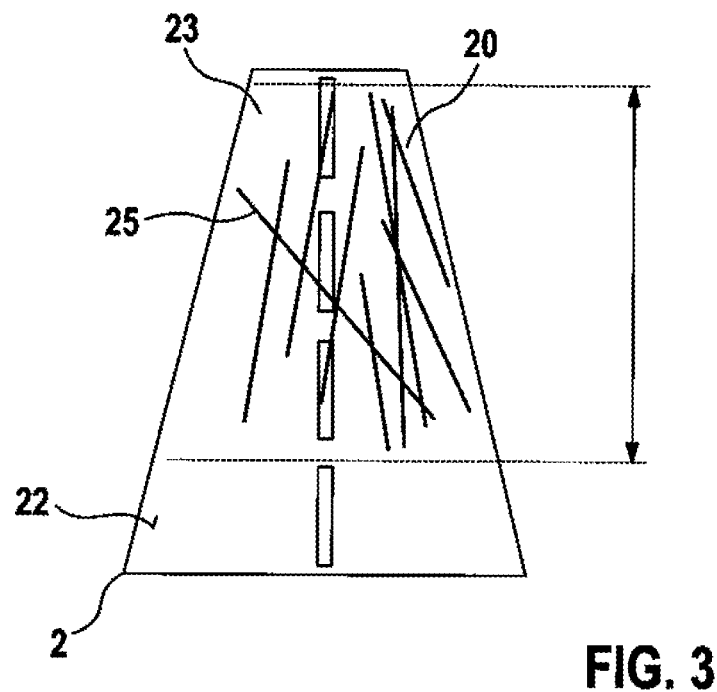
FIG. 3 shows an image pattern according to a specific embodiment.

According to the specific embodiment of FIG. 3, light pattern 20 has multiple, here, for example, nine, pattern characteristics 25 which, in the shown specific embodiment, are lines 25. Lines 25 are in particular straight lines 25, advantageously delimited lines 25 or line sections (distances). Light pattern 20 is advantageously not rotationally symmetrical or mirror symmetrical so that light pattern 20 may be detected from the opposite side, i.e., for example, by an oncoming vehicle, not as its own light pattern. Advantageously, for example, other road users coming from a crossing roadway may also not detect light pattern 20 emitted by vehicle 1 as their own, as light pattern 20 has no rotational symmetrical position and is therefore unambiguous. Furthermore, light pattern 20 enables an unambiguous detection and assignment of individual lines 25 not only from the length of individual lines 25 but also from the angles of lines 25.

Subsequently, control device 26 evaluates light pattern 20, namely, on the one hand, the geometrical structure of lines 25, and, on the other hand, the intensity or brightness of light pattern 20, the brightness of the recorded lines or pattern characteristics 25 and of the other areas being recordable and comparable. Reflectance r of roadway surface 22 may thus be ascertained and assigned unambiguously to different classes with predefined values for comparison.

Such classes to which roadway surface 22 may be assigned are in particular the following classes:
k0: asphalt,
k1: wet from rain or water film,
k2: light frost, cloudy frost,
k3: black ice, freezing moisture,
k4: snow,
k5: gravel, dirt and other structurings which considerably widen the lines in their geometry.

These classes are advantageously assigned reflectances r1 through r4 or r5 which may correspond, for example, to the following values:
r_ice of frost or ice,
r0 of asphalt,
r_H2O of water,
r_ice_1 of cloudy frost,
r_ice_2 of freezing moisture or black ice,
r_ice_3 of snow.

Corresponding friction coefficients μ may in turn be assigned to these reflectances.

Light pattern 20 may be interpreted individually, for example, for each vehicle type. For example, the wavelengths may be varied for different detection systems 3 and/or light pattern 20 or the arrangement of pattern characteristics 25 may be modified.

False lights which are generated by reflections off preceding vehicles or other obstacles may be detected by evaluating light pattern 20, in particular the geometry, i.e., the length of individual lines 25 and their angles in light pattern 20 so that it may be detected unambiguously whether light pattern 20 was reflected off a flat roadway 2.

Furthermore, the signal strength of light pattern 20 may subsequently be examined for whether it was reflected by a direct reflection off a preceding vehicle or another obstacle.

According to the light pattern of FIG. 3, lines 25 run essentially in traveling direction F, or entirely or partially in traveling direction F. A light pattern 20 is thus generated having lines 25 running into the distance.

The use of straight lines 25 has the advantage that these may be differentiated in light pattern 20 more clearly from other patterns and that interferences may be directly detected and ascertained.

In the case of reflections off a preceding vehicle or an obstacle, lines 25 in light pattern 20 are, for example, bent or their course and their angles to one another no longer correspond to typical light pattern 20 which is stored, for example, as a reference image and/or stored in control device 26.

Control device 26 thus activates pattern generator 14 with control signals S1 and evaluates image signals S2 of camera 12. In this process, angle of incidence α is selected in such a way that light pattern 20, for example, is provided in the lower image half or in a lower part of the image and does not interfere with the detection of the surroundings of vehicle 1, in particular characteristics in the upper image area. Camera 12 may in particular be designed as a stereo camera system in which distances may be directly ascertained using stereo measurement or triangulation.

Detection system 3 is advantageously calibrated in advance, two calibrations being advantageous:

As a first calibration, a geometrical calibration of the intrinsic camera parameters takes place for an optical model for calculating spaces and distances of the recorded road scene. It is thus possible to directly infer respective distance d to vehicle 1 from light pattern 20 or pattern characteristics 25, for example, the straight lines. According to the present invention it is detected that a calibration is here advantageous compared to a purely theoretical calculation due to the design of diffractive optical element 18 or projection lens 17.

Furthermore, a calibration advantageously takes place regarding signal strengths or intensities of retroreflected light 21. With this radiometric calibration, an absolute evaluation of the light intensity of the ascertained light pattern 20 against reflectances r of roadway surface 22 may take place.

Advantageously, the different reflectances r of roadway surfaces, i.e., r1, r2, r3, r4, r5 of the different classes k1, k2, k3, k4, k5 are stored in control device 26 or in a connected memory.

Control device 26 serves as control and evaluation device and evaluates in particular the following characteristics, i.e., it may advantageously carry out the following assessment steps:

Assessment Step a):

Control device 26 ascertains the signal strength or gray scale values of light pattern 20 and measures and assesses chronological changes of the signal strength of light pattern 20 or of retroreflected light 21.

Assessment Step b):

Control device 26 determines entire light pattern 20 in a space-resolved manner with regard to the signal strength and thus reflectance r in a space-resolved manner based on the gray scale values and the radiometrical calibration of camera 12.

Assessment Step c):

From the gray scale values and the geometrical calibration, distance d, i.e., the distances of the ascertained characteristics, to vehicle 1 may be ascertained.

Assessment Step d):

Based on the gray scale values, the radiometrical calibration and the geometrical calibration, the signal strength of the pattern or individual points of the pattern may be assigned to a distance d, i.e., to a distance d from the vehicle.

Assessment Step e):

From assessment step d) and stored values therefrom, in particular a stored table, for example, a look-up table, or stored reference values, the signal of light pattern 20 may assign in a space-resolved manner a reflectance r to roadway 2 in the image plane and in the object space, i.e., the street scene or lit area 23.

A space-resolved reflectance r or r as a function of distance d as well as also in transverse direction y may thus be ascertained in a resolved way.

Assessment Step f):

From assessment step e), control device 26 may calculate a probability of whether retroreflected light 21 was reflected by an obstacle or by roadway 2.

Assessment Step g):

From assessment step f), control device 26 may ascertain the probability for a class of different roadway surfaces 22, i.e., an assignment to classes k1 through k5, and thus ascertain different possibilities of iciness and ice values. As a consequence, control device 26 may output an evaluation signal S3 to the driver and/or to a vehicle control system. Evaluation signal S3 may be, for example, a warning signal for the driver or contain friction coefficient information.

Classification into k0 through k5 and thus different friction coefficients μ may then be used in a vehicle control system including a vehicle dynamics control system 30 for a vehicle control or vehicle dynamics control, for example, ABS and/or an electronic stability program as a function of the friction coefficient.

Figure 5:
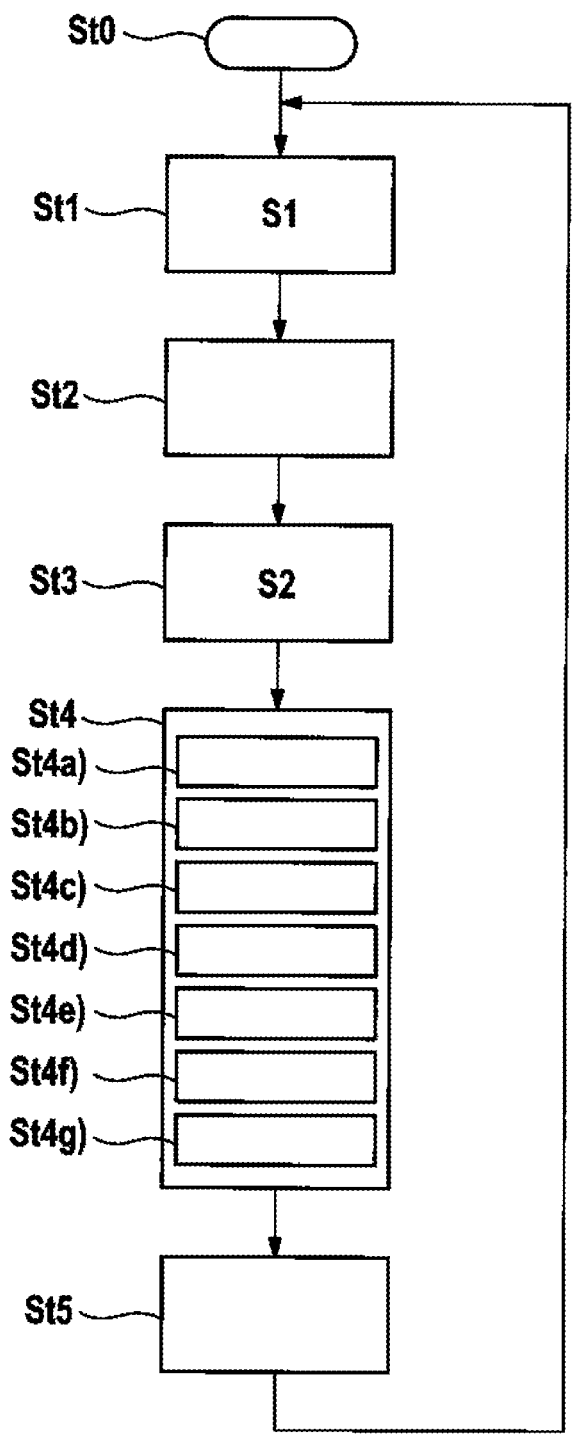
FIG. 5 shows a flow chart of a method according to the present invention.

The method according to the present invention thus provides the following steps according to the flow chart of FIG. 5:

After the start at step St0, control device 26 outputs control signal S1 to pattern generator 14,
in step St2, pattern generator 14 generates light signal 11 having light structures 19 using its LED 16 and projection lens 17, and sends it at an angle of incidence α onto roadway 22,
in step St3, camera 12 receives reflected radiation 21 of the same wavelength range as the wavelength range of emitted light signal 11 and outputs an image signal S2,
in step St4 the assessment steps a through g are carried out in order to evaluate roadway surface 22 of lit area 23 of roadway 2, and
in step St5, the signals are output, for example, for display to the driver and/or to a vehicle dynamics control system.

What is claimed is:

1. A method for detecting a roadway of a vehicle, comprising:
generating a light signal having light structures;
emitting the light signal onto the roadway;
receiving reflected radiation of the light signal off at least the roadway;
generating a light pattern as a function of the received reflected radiation;
evaluating the light pattern;
during the evaluating, detecting pattern characteristics of the light pattern that correspond to at least some of the light structures of the light signal;
analyzing a geometry of the detected pattern characteristics; and
inferring a surface of the roadway based at least on the analyzing.

2. The method as recited in claim 1, wherein the pattern characteristics are lines, and
wherein the lines are disposed at lengths and angles such that each line intersects with at least one other line.

3. The method of claim 2 wherein analyzing the geometry of the detected pattern characteristics comprises analyzing the lengths of the lines.

4. The method of claim 2 wherein analyzing the geometry of the detected pattern characteristics comprises analyzing the angles of the lines.

5. The method as recited in claim 1, wherein the light pattern is rotationally asymmetrical.

6. The method as recited in claim 1, wherein the light signal has a wavelength range below visible light.

7. The method as recited in claim 6, wherein the wavelength range is in a range of 780 nm to 820 nm.

8. The method as recited in claim 1, wherein the inferring is based at least on stored values of a radiometrical calibration from one of:
   a signal strength of the detected pattern characteristics; and
   a gray scale value of the light pattern.

9. The method as recited in claim 1, wherein the analyzing is based at least on one of:
   stored values of a geometrical calibration; and
   a stored pattern of the light pattern.

10. The method as recited in claim 1, further comprising ascertaining a probability from the light pattern whether a retroreflected light was emitted by one of:
    the roadway; and
    an obstacle.

11. The method as recited in claim 1, wherein the light pattern is classified in a space-resolved manner into at least one following class:
    asphalt;
    one of a film of water and a wetness from rain;
    frozen water including one of frost, ice, and snow; and
    one of gravel and dirt.

12. The method as recited in claim 11, wherein when the light pattern is classified as frozen water, a sub-classification into different subclasses takes place, into at least two of the following subclasses:
    one of light frost and cloudy frost; and
    one of black ice and freezing moisture.

13. The method as recited in claim 11, further comprising assigning one of friction coefficients and probability values of the friction coefficients to the classified light pattern.

14. The method of claim 1 wherein the pattern of the pattern characteristics is assigned to the vehicle.

15. The method of claim 1 further comprising:
    analyzing a signal strength of the detected pattern characteristics.

16. The method of claim 1 further comprising:
    analyzing a reflecting behavior of the detected pattern characteristics.

17. A detection system of a vehicle, comprising:
    a pattern generator, which generates and emits a light signal having light structures onto a roadway of the vehicle;
    a camera, which records radiation of the light signal that is reflected by at least the roadway, wherein:
       the pattern generator includes an LED device and a projection lens, which emits the light signal, and
       the projection lens has a diffractive optical element; and
    a control device, wherein the control device generates a light pattern as a function of the recorded radiation, wherein the control device also evaluates the light pattern by detecting pattern characteristics in the light pattern that correspond to at least some of the light structures of the light signal, wherein the control device determines a geometry of the detected pattern characteristics, wherein the control device analyzes a signal strength of the detected pattern characteristics, and wherein the control device infers a surface of the roadway from at least the analyzing.

18. A method for dynamically controlling a vehicle as a function of a friction coefficient of a roadway upon which the vehicle is travelling, comprising:
    generating a light signal having light structures;
    emitting the light signal onto the roadway;
    receiving reflected radiation of the light signal off at least the roadway;
    generating a light pattern as a function of the received reflected radiation;
    evaluating the light pattern;
    during the evaluating, detecting pattern characteristics of the light pattern that correspond to at least some of the light structures of the light signal;
    determining a geometry of the detected pattern characteristics;
    analyzing a signal strength of the detected pattern characteristics;
    inferring the friction coefficient of the roadway based at least on the analyzing; and
    dynamically controlling the vehicle, by a vehicle dynamics control system, at least in response to the determined geometry and the inferred friction coefficient.

19. A vehicle system, comprising:
    a detection system, including:
       a pattern generator, which generates and emits a light signal having light structures onto a roadway of the vehicle;
       a camera, which records radiation of the light signal that is reflected by at least the roadway, wherein:
          the pattern generator includes an LED device and a projection lens, which emits the light signal, and
          the projection lens has a diffractive optical element;
       a control device, wherein the control device generates a light pattern as a function of the recorded radiation, wherein the control device also evaluates the light pattern by detecting pattern characteristics in the light pattern that correspond to at least some of the light structures of the light signal, wherein the control device determines a geometry of the detected pattern characteristics, wherein the control device analyzes a signal strength of the detected pattern characteristics, and wherein the control device infers a surface of the roadway from at least the analyzing; and
    a vehicle dynamics control system, which dynamically controls the vehicle at least in response to the determined geometry and the inferred surface of the roadway.

20. The vehicle system as recited in claim 19, wherein the inferred surface of the roadway is a space-resolved classification of the roadway into values of one of iciness coefficients and friction coefficients.

* * * * *